(12) United States Patent
Albertson et al.

(10) Patent No.: US 7,677,086 B2
(45) Date of Patent: Mar. 16, 2010

(54) ENGINE OIL VISCOSITY DIAGNOSTIC SYSTEMS AND METHODS

(75) Inventors: William C. Albertson, Clinton Township, MI (US); David R. Staley, Flushing, MI (US); Mike M. McDonald, Macomb, MI (US); Bryan K. Pryor, Pontiac, MI (US)

(73) Assignee: GM Global Technology Operations, Inc., Detroit, MI (US)

( * ) Notice: Subject to any disclaimer, the term of this patent is extended or adjusted under 35 U.S.C. 154(b) by 404 days.

(21) Appl. No.: 11/684,952

(22) Filed: Mar. 12, 2007

(65) Prior Publication Data

US 2008/0223114 A1 Sep. 18, 2008

(51) Int. Cl.
*G01N 11/06* (2006.01)

(52) U.S. Cl. ..................... 73/54.02; 73/54.01

(58) Field of Classification Search ............... 73/54.01, 73/54.02
See application file for complete search history.

(56) References Cited

U.S. PATENT DOCUMENTS 6,591,798 B2 * 7/2003 Hendriksma et al. ..... 123/90.16

OTHER PUBLICATIONS

Han, T. et al., "Engine Oil Viscometer Based on Oil Pressure Sensor", SAE Technical Paper Series, 2006-01-0701, 2006 World Congress, Apr. 3-6, 2006, pp. 1-9.*

* cited by examiner

*Primary Examiner*—Daniel S Larkin

(57) ABSTRACT

An engine oil viscosity measurement system is provided. The system includes: a solenoid response module that determines an actual response time based on a position signal; an expected response module that determines an expected response time based on a system voltage and engine oil temperature; and a diagnostic module that diagnoses viscosity of the engine oil based on the actual response time and the expected response time.

21 Claims, 5 Drawing Sheets

ENGINE OIL VISCOSITY DIAGNOSTIC SYSTEMS AND METHODS

FIELD

The present disclosure relates to engine control systems and methods.

BACKGROUND

The statements in this section merely provide background information related to the present disclosure and may not constitute prior art.

Motor oil is a type of liquid oil used for lubrication by various types of motors. In particular, internal combustion engines use motor oil to provide lubrication between mechanical components. The motor oil also serves as a cooling system to the engine. The motor oil dissipates heat generated by friction between the mechanical components.

Oil viscosity is the ability of oil to flow and is expressed as a proportionality constant between the shear stress and shear rate of a fluid. Viscosity is typically affected by temperature, chemical properties, and other constituents in the oil. Viscosity influences the oil's ability to flow which in-turn influences the motivating force, or pressure, required to push the oil sufficiently to develop the necessary flow. For example, hot oil flows faster than cold oil, which can influence operating pressure characteristics of the system. The rate of oil flow is important to the life of an engine. Previously, engine oil viscosity was of interest only to provide good hydrodynamic lubrication of load-bearing surfaces and to assure adequate flow throughout the engine. With recent advancements in engine controls that use engine oil for precise timing, oil viscosity has become increasingly important. Such advancements include cam phasing, active fuel management, and two-step valve actuation. These are all positive displacement devices that require an oil flow source to develop sufficient pressure which provides hydraulic actuation of components within an engine. Thus, their function can be sensitive to the viscosity characteristics of the oil. Engine oil viscosity can be difficult to forecast due to the variability of oil change intervals associated with driving conditions as well as various oil chemistries, and aftermarket oil additives.

Providing a control system to diagnose the viscosity of the engine oil would enhance the operation of engine components that rely on the engine oil.

SUMMARY

Accordingly, an engine oil viscosity diagnostic system is provided. The system includes: a solenoid response module that determines an actual response time based on a position signal; an expected response module that determines an expected response time based on a system voltage and engine oil temperature; and a diagnostic module that diagnoses viscosity of the engine oil based on the actual response time and the expected response time.

In other features, an engine system for diagnosing engine oil viscosity is provided. The system includes: an engine oil sump that stores engine oil; a solenoid disposed within the engine oil sump; a solenoid sensor that generates a solenoid signal; and a control module that determines an actual response time based on the solenoid signal, determines an expected response time based on system voltage and engine oil temperature, and diagnoses viscosity of the engine oil based on the expected response time and the actual response time.

In still other features, a method of diagnosing engine oil viscosity is provided. The method includes: determining an actual response time of a solenoid based on a trigger event and solenoid current; determining an expected response time based on system voltage and engine oil temperature; and diagnosing viscosity of the engine oil based on the actual response time and the expected response time.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
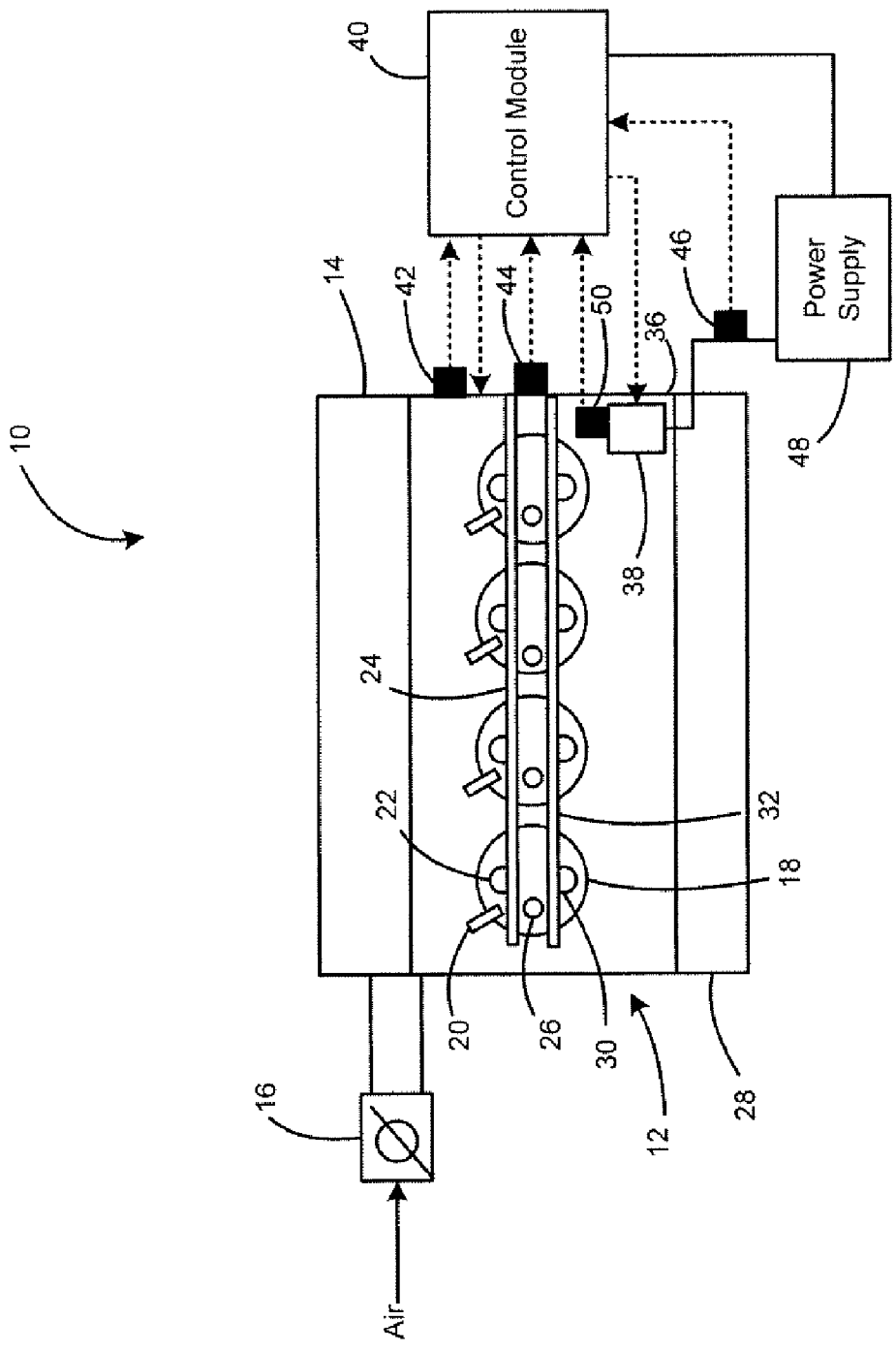
FIG. 1 is a functional block diagram illustrating an exemplary engine system.

The following description is merely exemplary in nature and is not intended to limit the present disclosure, application, or uses. It should be understood that throughout the drawings, corresponding reference numerals indicate like or corresponding parts and features. As used herein, the term module refers to an application specific integrated circuit (ASIC), an electronic circuit, a processor (shared, dedicated, or group) and memory that executes one or more software or firmware programs, a combinational logic circuit, and/or other suitable components that provide the described functionality.

Referring now to FIG. 1, an exemplary engine system 10 includes an engine 12 that combusts an air and fuel mixture to produce drive torque. Air is drawn into an intake manifold 14 through a throttle 16. The throttle 16 regulates mass air flow into the intake manifold 14. Air within the intake manifold 14 is distributed into cylinders 18. Although four cylinders 18 are illustrated, it can be appreciated that the engine 12 can have a plurality of cylinders including, but not limited to, 2, 3, 5, 6, 8, 10, 12 and 16 cylinders. Although the cylinders 18 are shown to be in an inline configuration, it can be appreciated that the cylinders 18 can alternatively be in a V-shaped configuration.

A fuel injector 20 injects fuel that is combined with the air as it is drawn into the cylinder 18 through an intake port. An intake valve 22 selectively opens and closes to enable the air/fuel mixture to enter the cylinder 18. The intake valve position is regulated by an intake camshaft 24. A piston (not shown) compresses the air/fuel mixture within the cylinder 18. A spark plug 26 initiates combustion of the air/fuel mixture, driving the piston in the cylinder 18. The piston drives a crankshaft (not shown) to produce drive torque. Combustion exhaust within the cylinder 18 is forced out through an exhaust manifold 28 when an exhaust valve 30 is in an open position. The exhaust valve position is regulated by an exhaust camshaft 32. The exhaust is treated in an exhaust system. Although single intake and exhaust valves 22,30 are illustrated, it can be appreciated that the engine 12 can include multiple intake and exhaust valves 22,30 per cylinder 18.

An engine oil sump 36 couples to the engine 12 and serves as a reservoir for engine oil. An engine oil pump (not shown) circulates oil through passages of the engine 12 to provide sufficient pressure for hydraulic function as well as lubrication and cooling for the engine 12. A viscosity sensitive solenoid 38 is disposed within the engine oil sump 36, just below a liquid level. A control module 40 controls the solenoid 38 and diagnoses engine oil viscosity based on one or more sensory inputs. More particularly, an oil temperature sensor 42 or equivalent algorithm generates an oil temperature signal based on a temperature of oil within the engine 12. An engine speed sensor 44 generates an engine speed signal based on a rotational speed of the crankshaft (not shown). A voltage sensor 46 senses a voltage of the engine system 10 provided by a power source 48. A current sensor 50 measures the current of the solenoid 38 and generates a current signal. Alternatively, a Hall effect sensor senses a changing magnetic flux of the solenoid 38 or a position sensor senses a position of an armature 54 (FIG. 2) of the solenoid 38 as will be discussed in further detail below. The control module 40 receives the above mentioned signals and diagnoses engine oil viscosity as will be discussed in more detail below.

Figure 2:
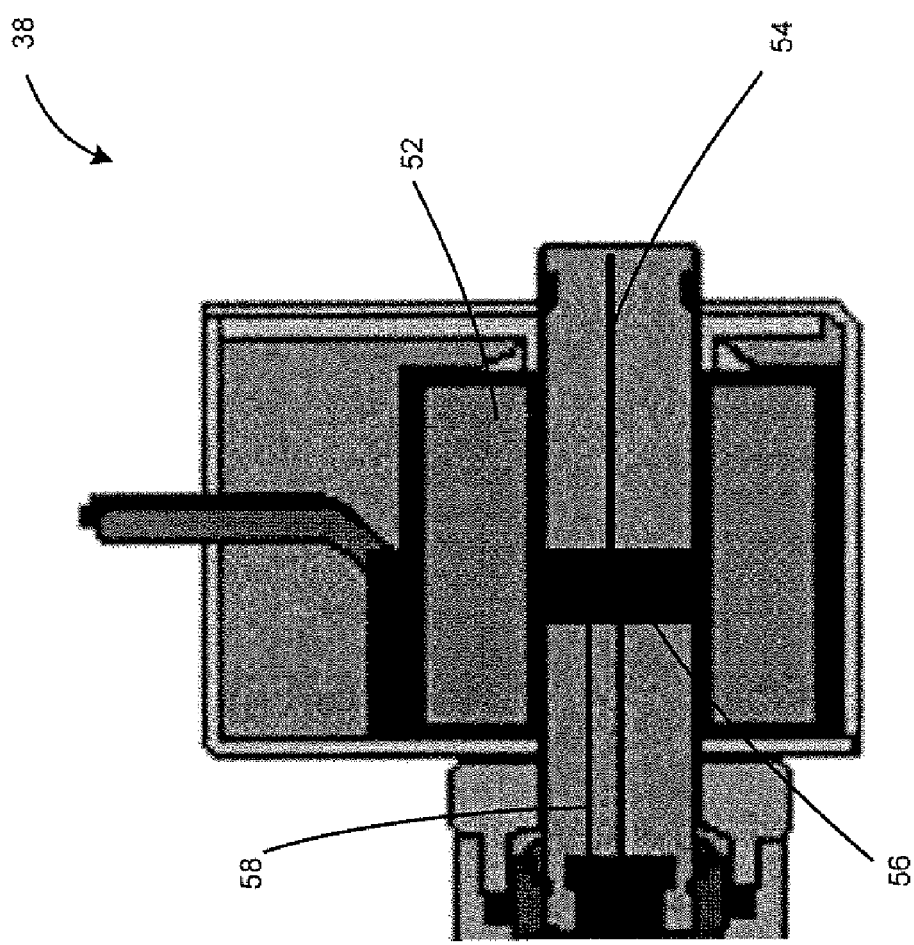
FIG. 2 is a cross-sectional view of an exemplary viscosity sensitive solenoid.

FIG. 2 is a cross-sectional view of an exemplary solenoid 38 having a viscosity sensitive oil flow damper that resides in the oil reservoir of the engine where ambient pressure acts uniformly on all components of the solenoid 38. The solenoid 38 generally includes an electromagnetic coil 52 and an armature 54 that is disposed coaxially within the coil 52. The armature 54 is biased to a first position relative to the coil 52 by a biasing force. The biasing force can be imparted by a biasing member, such as a spring (not shown in FIG. 2), or by a pressurized fluid. The solenoid 38 is energized by supplying current to the coil 52, which induces a magnetic force along the coil axis. The magnetic force induces linear movement of the armature 54 to a second position. When in the second position, a volume 56 of oil is displaced by the movement of the armature 54 through a viscosity sensitive orifice 58. The displacement of oil through the viscosity sensitive orifice 58 results in an increase in pressure within the volume 56. This pressure acting on the frontal area of the armature 54 creates a resistive force that slows its movement which in-turn alters the current draw characteristics of the solenoid 38. As can be appreciated, at least one of a current sensor, a Hall effect sensor, or a position sensor can be used to detect the movement of the armature 54. For ease of the discussion, the remainder of the disclosure will be discussed in the context of the current sensor measuring the current draw of the solenoid 38.

Figure 3:
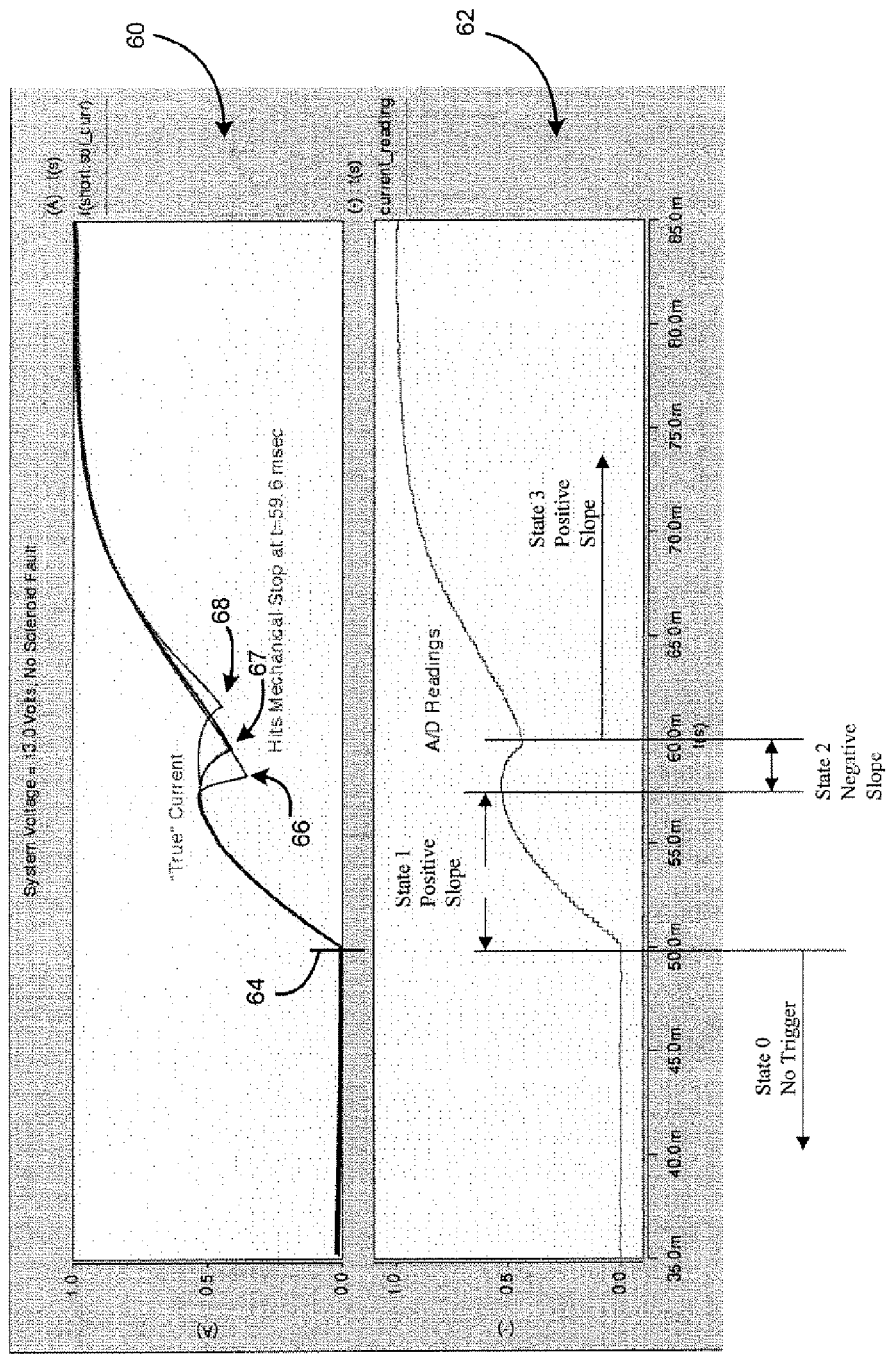
FIG. 3 is a graph illustrating current generated by a viscosity sensitive solenoid.

FIG. 3 is a graphical representation of current flowing through the solenoid 38. The top graph 60 corresponds to the actual current flowing through the solenoid 38 provided engine oil with three different viscosities. The bottom graph 62 corresponds to digital current readings. In both graphs 60 and 62, a trigger signal 64 occurs at approximately 50 ms and a "valley" shown generally at 66, 67, and 68 exists at approximately 60 ms. The "valley" 66 in the current readings corresponds to the armature 54 of the solenoid 38 hitting a mechanical stop. The time delay is the difference in time between the trigger signal 64 and the "valley" 66, 67, and 68 of the current readings.

In the bottom graph 62, state 0 describes the state of the solenoid 38 before the trigger signal 64 is commanded, state 1 describes the state of increasing solenoid current, state 2 describes decreasing solenoid current, and state 3 describes increasing solenoid current after the armature 54 of the solenoid 38 has hit the mechanical stop. The time delay is the time elapsed between the state 0 to state 1 transition and the state 2 to state 3 transition.

The time of the state 0 to state 1 transition is the time that the trigger signal 64 is activated. However, the time for the remaining transitions is calculated by inspection of the current signal. In state 1, the current signal increases and has a positive slope. In state 2, the current signal decreases and has a negative slope. The state 1 to state 2 transition is when the current slope changes from positive to negative. Since state 3 has an increasing slope, the state 2 to state 3 transition is determined by the time at which the current slope changes from negative to positive.

As is commonly known, the derivative of a function represents the slope of the function. In a discrete domain, an adequate approximation of the derivative of the current signal can be calculated in order to determine the slope. Several numerical methods may be employed to achieve this objective. The simplest is a two-point backward difference approximation of the derivative. The two-point backward difference approximation uses the following equation:

$$y' = \frac{y_n - y_{n-1}}{h}$$

where y' is the approximate derivative of the current signal, $y_n$ is the present sample of the current signal, $y_{n-1}$ is the previous sample of the current signal, and h is the time between samples of the current signal.

The two-point backward difference approximation of the derivative may be sensitive to signal noise. Approximations with a smaller degree of error can be calculated, but they generally use additional samples to achieve accuracy or use non-realtime processing. Therefore, it is preferable to calculate the derivative of a moving average of the current signal rather than the current signal directly. Although the moving average of the samples will help smooth out noise, it is still possible for slight increases and decreases in the derivative of the slope to prematurely indicate that the current signal has changed direction. Thus, it is preferable for a change in slope to persist for several consecutive samples before it is reported. If the state 2 to state 3 transition is not detected within a predetermined period, a maximum time (e.g., 50 ms) is reported as the response time of the solenoid 38.

Figure 4:
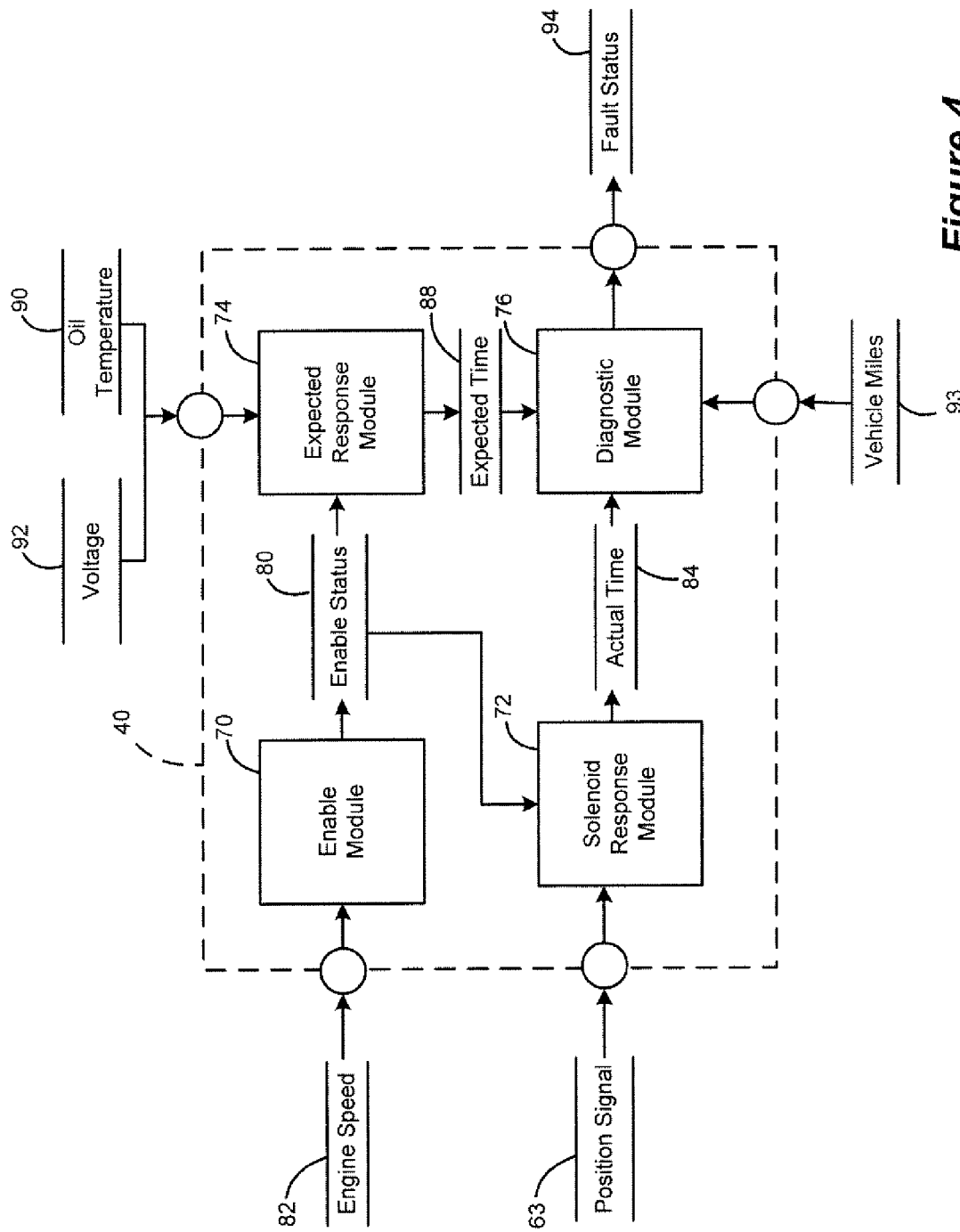
FIG. 4 is a dataflow diagram illustrating an engine oil viscosity diagnostic system.

Referring now to FIG. 4, a dataflow diagram illustrates various embodiments of an engine oil viscosity diagnostic system that may be embedded within the control module 40. Various embodiments of engine oil viscosity diagnostic systems according to the present disclosure may include any number of sub-modules embedded within the control module 40. The sub-modules shown may be combined and/or further partitioned to similarly control the engine 12. Inputs to the engine oil viscosity diagnostic system may be sensed from the engine system 10 (FIG. 1), received from other control modules (not shown), and/or determined by other sub-modules (not shown) within the control module 40. In various embodiments, the control module 40 of FIG. 4 includes an enable module 70, a solenoid response module 72, an expected response module 74, and a diagnostic module 76.

The enable module 70 selectively enables the solenoid control via an enable status indicator 80. The enable module 70 selectively enables solenoid control based on engine speed 82. If engine speed is zero or the engine speed is steady, the enable module 70 sets the enable status 80 to TRUE. Otherwise, the enable status 80 remains set to FALSE. The solenoid response module 72 measures an actual response time 84 based on a position signal 63. The position signal 63 can indicate at least one of a solenoid current, an armature position, and a magnetic flux. The solenoid response module 72 measures an actual response time 84 by monitoring the position signal 63. In various embodiments, the solenoid response module 72 measures an actual response time 84 by monitoring a solenoid current and determining a time between an electrical trigger event to the current valley as discussed above.

The expected response module 74 predicts an expected response time 88 based on system voltage 92 and oil temperature 90. In various embodiments, the expected response time 88 is predicted based on a predefined lookup table that is stored in memory. The indices of the table are system voltage 92 and oil temperature 90. The response times for selected system voltage and oil temperature are predefined based on particular oil viscosities. In various embodiments, the expected response times are initially based on properties of factory fill oil.

The diagnostic module 76 diagnoses the engine oil viscosity based on the actual response time 84 and the expected response time 88. The diagnostic module 76 computes a difference between the actual response time 84 and the expected response time 88, divides the difference by the expected response time 88 to determine a percent error. The diagnostic module compares the percent error to a threshold percentage. If the percent error is greater than the threshold percentage, a fault status 94 is set to Test Fail. If the percent error is less than or equal to the threshold percentage of the expected response time, the fault status 94 is set to Test Pass. In various embodiments, if the percent error is less than the threshold percentage and a total of vehicle miles 93 is less than a mile threshold, the diagnostic module 76 adapts the expected response time based on the percent error and stores the adapted expected response time in memory for later use. Either additionally or alternatively, if the percent error is less than the threshold percentage and oil life (not shown) is less than a threshold percentage, the diagnostic module 76 adapts the expected response time based on the percent error and stores the adapted expected response time in memory for later use.

Figure 5:
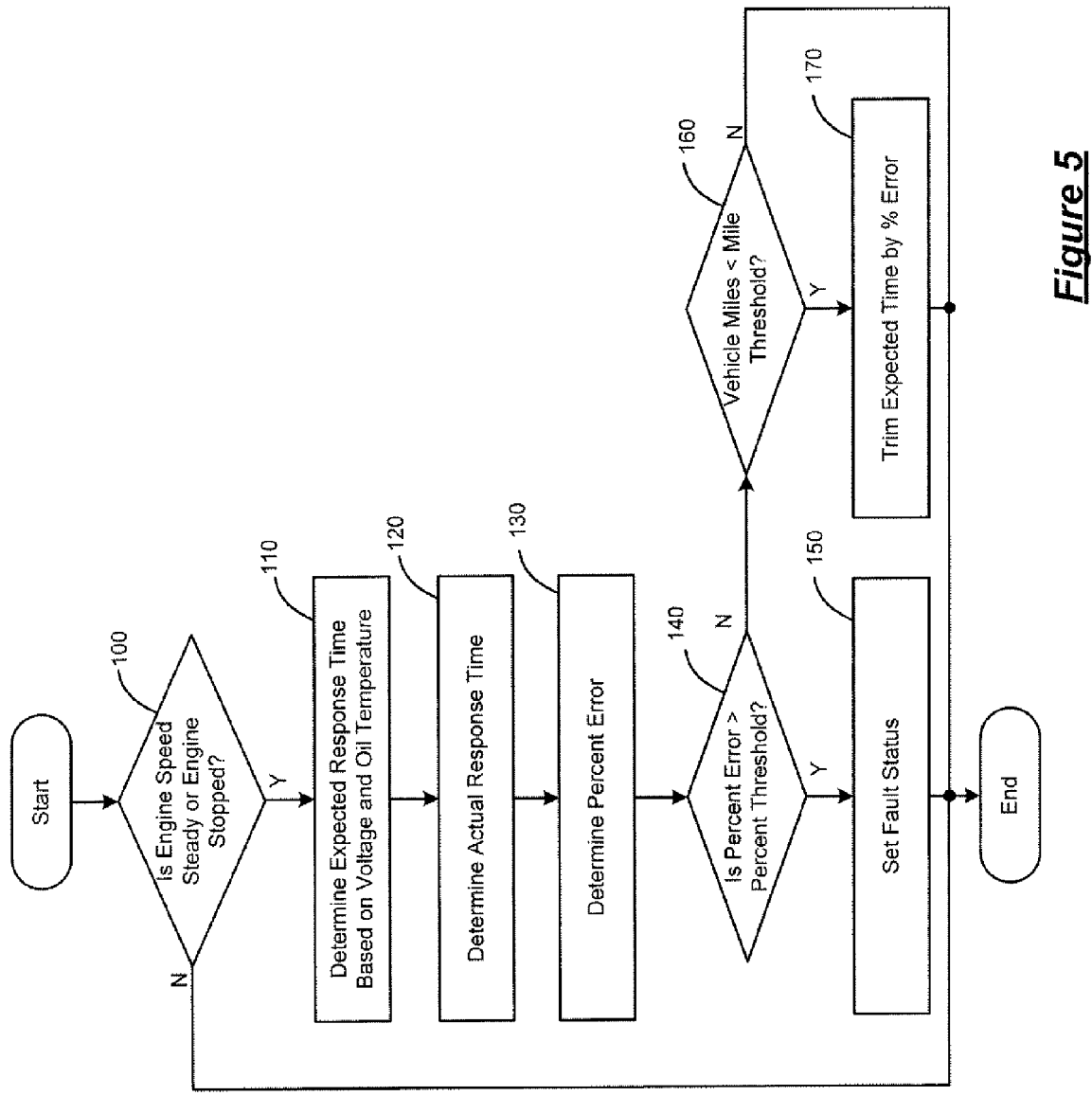
FIG. 5 is a flowchart illustrating an engine oil viscosity diagnostic method.

Referring now to FIG. 5, a flowchart illustrates various embodiments of an engine oil viscosity measurement method that may be performed by the control module 40. The method may be run periodically during engine operation. At 100, enable conditions are evaluated. If the engine speed is steady or the engine speed is zero at 100, the expected response time is determined at 110. Otherwise, control proceeds to the end. At 110, the expected response time is determined based on system voltage and oil temperature. At 120, the actual response time is determined. At 130, a percent error is determined based on the difference between the expected response time and the actual response time. The percent error is evaluated at 140. If the percent error is greater than a predetermined error threshold at 140, the fault status is set to Test Fail at 150. Otherwise if the percent error is less than a predetermined error threshold at 140, the total vehicle miles is evaluated at 160. If the total of vehicle miles is less than a mile threshold at 160, the expected response time is trimmed by the percent error and stored in memory at 170. Otherwise, if the total of vehicle miles is greater than or equal to the mile threshold at 160, control proceeds to the end.

As can be appreciated, once the fault status is set to Test Fail, additional steps can be performed to notify other systems and users of the failure. In various embodiments, a diagnostic code is set based on the fault status. The diagnostic code can be retrieved by a service tool or transmitted to a remote location via a telematics system. In various other embodiments, an indicator lamp is illuminated based on the fault status. In various other embodiments, an audio warning signal is generated based on the fault status or the engine's hydraulic control function may be limited.

As can be appreciated, all comparisons discussed above can be implemented in various forms depending on the selected values for comparison. For example, a comparison of "greater than" may be implemented as "greater than or equal to" in various embodiments. Similarly, a comparison of "less than" may be implemented as "less than or equal to" in various embodiments. A comparison of "within a range" may be equivalently implemented as a comparison of "less than or equal to a maximum threshold" and "greater than or equal to a minimum threshold" in various embodiments.

Those skilled in the art can now appreciate from the foregoing description that the broad teachings of the present disclosure can be implemented in a variety of forms. Therefore, while this disclosure has been described in connection with particular examples thereof, the true scope of the disclosure should not be so limited since other modifications will become apparent to the skilled practitioner upon a study of the drawings, specification, and the following claims.

What is claimed is:

1. An engine oil viscosity diagnostic system, comprising:
   a solenoid response module that determines an actual response time based on a position signal;
   an expected response module that determines an expected response time based on system voltage and engine oil temperature; and
   a diagnostic module that diagnoses viscosity of the engine oil based on the actual response time and the expected response time.

2. The system of claim 1 wherein the position signal indicates solenoid current and wherein the solenoid response module determines the actual response time by computing a difference between a time of a trigger event and a time when solenoid current exceeds a current threshold.

3. The system of claim 1 wherein the expected response module determines the expected response time by interpolating the expected response time from a lookup table accessed by system voltage and engine oil temperature.

4. The system of claim 1 wherein the diagnostic module computes a percent error based on the expected response time and the actual response time and diagnoses the engine oil viscosity based on the percent error.

5. The system of claim 1 wherein the diagnostic module adapts the expected response time based on a percent error.

6. The system of claim 1 wherein the diagnostic module sets a fault status indicator based on the viscosity.

7. The system of claim 6 wherein the diagnostic module modifies the expected response time by the percent error when a total of vehicle miles is less than a mile threshold.

8. The system of claim 1 further comprising an enable module that enables the solenoid response module and the expected response module to determine the actual response time and the expected response time respectively based on engine speed.

9. The system of claim 1 wherein the position signal indicates at least one of a solenoid armature position, a solenoid current, and a magnetic flux.

10. An engine system for diagnosing engine oil viscosity, comprising:
    an engine oil sump that stores engine oil;
    a solenoid disposed within the engine oil sump;
    a solenoid sensor that generates a solenoid signal; and a control module that determines an actual response time based on the solenoid signal, determines an expected response time based on system voltage and engine oil temperature, and diagnoses viscosity of the engine oil based on the expected response time and the actual response time.

11. The system of claim 10 wherein the solenoid is a viscosity sensitive solenoid.

12. The system of claim 10 wherein the solenoid is disposed within the engine oil sump below an oil level.

13. The system of claim 10 wherein the solenoid sensor generates a solenoid signal based on at least one of a magnetic flux, a position, and a current.

14. A method of diagnosing engine oil viscosity, comprising:
   determining an actual response time of a solenoid based on a trigger event and solenoid current;
   determining an expected response time based on system voltage and engine oil temperature; and
   diagnosing viscosity of the engine oil based on the actual response time and the expected response time.

15. The method of claim 14 wherein the determining actual response time further comprises determining the actual response time by computing a difference between a time of the trigger event and a time when the solenoid current exceeds a current threshold.

16. The method of claim 14 wherein determining the expected response time further comprises interpolating the expected response time from a lookup table wherein the lookup table is accessed by system voltage and engine oil temperature.

17. The method of claim 14 further comprising computing a percent error based on the expected response time and the actual response time and wherein the diagnosing the engine oil viscosity is based on the percent error.

18. The method of claim 17 further comprising adapting the expected response time by the percent error.

19. The method of claim 18 wherein the adapting the expected response time further comprises adapting the expected response time by the percent error when a total of vehicle miles is less than a mile threshold.

20. The method of claim 14 further comprising setting a fault status indicator based on the diagnosing the viscosity.

21. The method of claim 14 further comprising enabling the determining the actual response time and the determining the expected response time based on engine speed.

* * * * *